US012630848B2

(12) United States Patent
Takahashi et al.

(10) Patent No.: US 12,630,848 B2
(45) Date of Patent: May 19, 2026

(54) METHOD FOR PRODUCING ETHANOL FROM LIGNOCELLULOSIC RAW MATERIAL

(71) Applicants: ENEOS Corporation, Tokyo (JP); Oji Holdings Corporation, Tokyo (JP)

(72) Inventors: Yuichi Takahashi, Tokyo (JP); Kohei Ide, Tokyo (JP); Masahiro Niwa, Tokyo (JP); Miyuki Kanezawa, Tokyo (JP); Shoichi Ikemizu, Tokyo (JP); Atsushi Furujo, Tokyo (JP); Naoya Azumi, Tokyo (JP); Akira Tsukamoto, Tokyo (JP); Shingo Sekizawa, Tokyo (JP)

(73) Assignees: ENEOS Corporation, Tokyo (JP); Oji Holdings Corporation, Tokyo (JP)

( * ) Notice: Subject to any disclaimer, the term of this patent is extended or adjusted under 35 U.S.C. 154(b) by 0 days.

(21) Appl. No.: 18/454,556

(22) Filed: Aug. 23, 2023

(65) Prior Publication Data

US 2023/0407347 A1     Dec. 21, 2023

Related U.S. Application Data

(62) Division of application No. 17/274,775, filed as application No. PCT/JP2019/035547 on Sep. 10, 2019, now Pat. No. 11,773,415.

(30) Foreign Application Priority Data

Sep. 10, 2018     (JP) ................................. 2018-169163

(51) Int. Cl.
| | |
|---|---|
| *C12P 7/08* | (2006.01) |
| *C12N 9/24* | (2006.01) |
| *C12N 9/42* | (2006.01) |
| *C12P 7/10* | (2006.01) |

(52) U.S. Cl.
CPC .................................... *C12P 7/08* (2013.01)

(58) Field of Classification Search
None
See application file for complete search history.

(56) References Cited

U.S. PATENT DOCUMENTS

| | | | |
|---|---|---|---|
| 9,593,355 | B2 | 3/2017 | Louret et al. |
| 11,773,415 | B2 | 10/2023 | Takahashi et al. |
| 2014/0377812 | A1 | 12/2014 | Louret et al. |
| 2015/0076078 | A1 | 3/2015 | Gallop |
| 2022/0049278 | A1 | 2/2022 | Takahashi et al. |

FOREIGN PATENT DOCUMENTS

| | | |
|---|---|---|
| CN | 103103220 A | 5/2013 |
| CN | 104862344 A | 8/2015 |
| JP | 2006-087319 A | 4/2006 |
| JP | 2011-223975 A | 11/2011 |
| JP | 2013-126395 A | 6/2013 |
| JP | 2014-090707 A | 5/2014 |
| JP | 2015-500038 A | 1/2015 |
| JP | 2016-028564 A | 3/2016 |
| WO | WO 2007/100897 A2 | 9/2007 |

OTHER PUBLICATIONS

English-language translation of JP 2014090707, 54 pages, obtained from Google Patents on Jul. 30, 2024 (Year: 2024).*
Xiao et al., "Effects of Sugar Inhibition on Cellulases and β-Glucosidase During Enzymatic Hydrolysis of Softwood Substrates," Applied Biochemistry and Biotechnology 115:1115-1126, 2004 (Year: 2004).*
Gurram et al., "Continuous Enzymatic Hydrolysis of Lignocellulosic Biomass with Simultaneous Detoxification and Enzyme Recovery", Appl. Biochem. Biotechnol. 173:1319-1335, 2014 (Year: 2014).*
English-language translation of JP 2016028564 A, 19 pages, obtained from Google Patents on Jun. 13, 2025 (Year: 2025).*
Ghose et al., "Simultaneous Saccharification and Fermentation (SSF) of Lignocellulosics to Ethanol Under Vacuum Cycling and Step Feeding," Biotechnol. Bioeng., 26(4): 377-381 (1984).
Leblanc et al., "Viscosity Measurement—Chapter 30.1: Shear Viscosity" in "Mechanical Variables Measurement—Solid, Fluid, and Thermal" (John G. Webster (editor)), CRC Press LLC, (1999).
Nakasaki et al., "Effects of Intermittent Addition of Cellulase for Production of $_L$-Lactic Acid From Wastewater Sludge by Simultaneous Saccharification and Fermentation," Biotechnol. Bioeng., 82(3): 263-270 (2003).
OJI Holdings Corporation, "Manufacture of Ethanol from Lignocellulosic Raw Material Involves Performing Saccharification and Fermentation of Lignocellulosic Raw Material," WPI/Clarivate Analytics Database Accession No. 2016-136996 (2016).
Olofsson et al., "Controlled feeding of cellulases improves conversion of xylose in simultaneous saccharification and co-fermentation for bioethanol production," J. Biotechnol., 145: 168-175 (2010).
Zhang et al., "Application of Simultaneous Saccharification and Fermentation (SSF) from Viscosity Reducing of Raw Sweet Potato for Bioethanol Production at Laboratory, Pilot and Industrial Scales," Bioresour. Technol., 102(6): 4573-4579 (2011).
China National Intellectual Property Office, Office Action in Chinese Patent Application No. 201980058741.6 (Apr. 20, 2023).

(Continued)

*Primary Examiner* — David Steadman
(74) *Attorney, Agent, or Firm* — Leydig, Voit & Mayer, Ltd.

(57) ABSTRACT

The present invention provides a method for efficiently producing ethanol from a lignocellulosic raw material. More specifically, the present invention provides a method for producing ethanol from a lignocellulosic raw material, which comprises a step of performing multiple parallel fermentation while continuously or intermittently adding an additional saccharification enzyme to a fermentation liquid comprising a lignocellulosic raw material, a saccharification enzyme and a yeast so that the physical property value of the fermentation liquid itself is maintained within a preset range.

16 Claims, 6 Drawing Sheets

(56)             References Cited

OTHER PUBLICATIONS

European Patent Office, Extended European Search Report in European Patent Application No. 19860285.6 (Jul. 18, 2022).

Indonesian Directorate General of Intellectual Property, Office Action in Indonesian Patent Application No. HKI-3-KI.05.01.08-TA-P00202102561 (Oct. 29, 2022).

Japanese Patent Office, Notice of Reasons for Refusal in Japanese Patent Application No. 2018-169163 (Feb. 15, 2022).

Japanese Patent Office, International Search Report in International Patent Application No. PCT/JP2019/035547 (Dec. 17, 2019).

The International Bureau of WIPO, International Preliminary Report on Patentability in International Patent Application No. PCT/JP2019/035547 (Mar. 9, 2021).

China National Intellectual Property Administration, Office Action in Chinese Patent Application No. 201980058741.6 (Nov. 30, 2023).

China National Intellectual Property Administration, Office Action in Chinese Patent Application No. 201980058741.6 (Apr. 16, 2024).

IP Australia, Examination Report in Australian Patent Application No. 2019340161 (Jun. 5, 2024).

European Patent Office, Communication pursuant to Article 94(3) EPC in European Patent Application No. 19860285.6 (Jan. 30, 2026).

Brazil National Institute of Industrial Property, Office Action in Brazil Patent Application No. BR112021004447-7 (Feb. 23, 2026).

* cited by examiner

METHOD FOR PRODUCING ETHANOL FROM LIGNOCELLULOSIC RAW MATERIAL

CROSS-REFERENCE TO RELATED APPLICATIONS

The present patent application claims priority to Japanese Patent Application No. 2018-169163 filed on Sep. 10, 2018, the entire contents of which are incorporated herein by reference.

TECHNICAL FIELD

The present invention relates to a method for producing ethanol from a lignocellulosic raw material.

BACKGROUND ART

A technology of producing saccharides from non-edible lignocellulosic raw materials is a technology extremely beneficial to the formation of a recycling-oriented society since it can produce alcohols that may be used as a gasoline substitute fuel by using, as fermentation substrates for microorganisms, the saccharides produced, and also can prevent competition with food.

There has been known, as the method for producing saccharides such as monosaccharides and oligosaccharides that serve as fermentation substrates from polysaccharides in lignocellulosic raw materials, an enzymatic saccharification method that hydrolyzes using saccharification enzymes such as cellulolytic enzymes and microorganisms that produce the saccharification enzymes.

Further, multiple parallel fermentation is known as a method for producing ethanol from lignocellulose by applying an enzymatic saccharification method. In the multiple parallel fermentation, ethanol-fermenting microorganisms are allowed to coexist with the above saccharification enzymes, and an enzymatic saccharification reaction and ethanol fermentation are simultaneously performed.

The production of ethanol from lignocellulosic raw materials by multiple parallel fermentation has a problem that the cost is high as compared with the production method using starch, molasses and the like as raw materials. Therefore, there has been studied a method for efficiently producing ethanol from lignocellulosic raw materials.

Patent Document 1 discloses a method comprising recovering an unreacted lignocellulose material and a saccharification enzyme from a continuous reaction solution, wherein using a lignocellulose material subjected to a lignin removal operation as a substrate, a ratio of the amount of the all substrates to the amount of the saccharification enzyme in a dispersion fed to a continuous saccharification reaction tank is maintained at a ratio at which at least 96% by mass of the all substrates is saccharified within a retention time, thereby continuously performing a saccharification reaction while preventing the accumulation of an unreacted lignocellulose.

However, there is still a need to efficiently produce ethanol from lignocellulosic raw materials.

RELATED ART DOCUMENTS

Patent Literature

Patent literature 1: JP 2006-087319 A

SUMMARY OF THE INVENTION

An object of the present invention is to efficiently produce ethanol. In particular, an object of the present invention is to maintain the concentration of ethanol to be produced above a certain level.

The present inventors have recently found that the concentration of ethanol produced in fermentation liquid comprising a lignocellulosic raw material, a saccharification enzyme and a yeast can be maintained above a certain level if multiple parallel fermentation is performed while continuously or intermittently adding an additional saccharification enzyme to the fermentation liquid. Further, they have also found that the physical property value of above fermentation liquid itself can be used as an index for the addition of the additional saccharification enzyme. The present invention is based on these findings.

The present invention includes the following [1] to [15].

[1]

A method for producing ethanol from a lignocellulosic raw material, comprising:

a step of performing multiple parallel fermentation while continuously or intermittently adding an additional saccharification enzyme to a fermentation liquid comprising a lignocellulosic raw material, a saccharification enzyme and a yeast so that the physical property value of the fermentation liquid itself is maintained within a preset range.

[2]

The method according to [1], wherein the physical property value of the fermentation liquid itself is ethanol concentration and/or viscosity.

[3]

The method according to [1] or [2], wherein the additional saccharification enzyme is added so that the ethanol concentration of the fermentation liquid is maintained at 80% or more relative to the ethanol concentration at a point in time of becoming a steady state after the start of fermentation.

[4]

The method for producing ethanol according to any one of [1] to [3], wherein the additional saccharification enzyme is added so that an enzyme basic unit in the fermentation liquid is maintained at 0.1 to 30% relative to the enzyme basic unit after 1 to 12 hours from the start of fermentation.

[5]

The method for producing ethanol according to any one of [1] to [4], wherein a mass ratio of the addition amount of the additional saccharification enzyme per day to the initial content of the saccharification enzyme in the fermentation liquid (the addition amount of the additional saccharification enzyme per day:the initial content of saccharification enzyme in the fermentation liquid) is 1:10 to 1:100.

[6]

The method for producing ethanol according to any one of [1] to [5], wherein the additional saccharification enzyme is added to the fermentation liquid in an amount of 20 U/L or less.

[7]

The method for producing ethanol according to any one of [1] to [6], wherein the additional saccharification enzyme is intermittently added every 2 to 192 hours.

3

[8]

The method for producing ethanol according to any one of [1] to [7], wherein the additional saccharification enzyme is added to the fermentation liquid when the viscosity of the fermentation liquid exceeds 140 cP.

[9]

The method for producing ethanol according to any one of [1] to [8], wherein the concentration of the lignocellulosic raw material in the fermentation liquid is adjusted so as to be maintained within a predetermined range.

[10]

The method for producing ethanol according to [9], wherein the concentration of the lignocellulosic raw material in the fermentation liquid is adjusted so as to be maintained at 5 to 30% by mass.

[11]

The method for producing ethanol according to any one of [1] to [10], wherein the multiple parallel fermentation is performed in at least two reaction tanks connected to each other.

[12]

The method for producing ethanol according to [11], wherein the at least two reaction tanks are connected in series.

[13]

The method for producing ethanol according to or [12], wherein the at least two reaction tanks comprise a first reaction tank which stores the fermentation liquid and in which the additional lignocellulosic raw material is continuously fed.

[14]

The method for producing ethanol according to any one of [11] to [13], wherein the at least two reaction tanks comprise a second reaction tank to which a part of the fermentation liquid is continuously transferred from the first reaction tank.

[15]

The method for producing ethanol according to any one of [1] to [14], which further comprises the following step:

a solid-liquid separation step of separating an aqueous ethanol solution from the fermentation liquid, wherein the step comprising transferring a solid content concentrated fermentation liquid to the reaction tank after separating the aqueous ethanol solution.

According to the present invention, ethanol can be efficiently produced by performing multiple parallel fermentation while continuously or intermittently adding an additional saccharification enzyme so that the physical property value of the fermentation liquid itself is maintained within a preset range. The present invention is advantageous in that the concentration of ethanol produced can be maintained above a certain level. Further, the present invention is advantageous in that the manufacturing cost can be reduced by extending the continuous operation time.

4 indicates a point in time of starting the addition of an additional saccharification enzyme.

Figure 4:
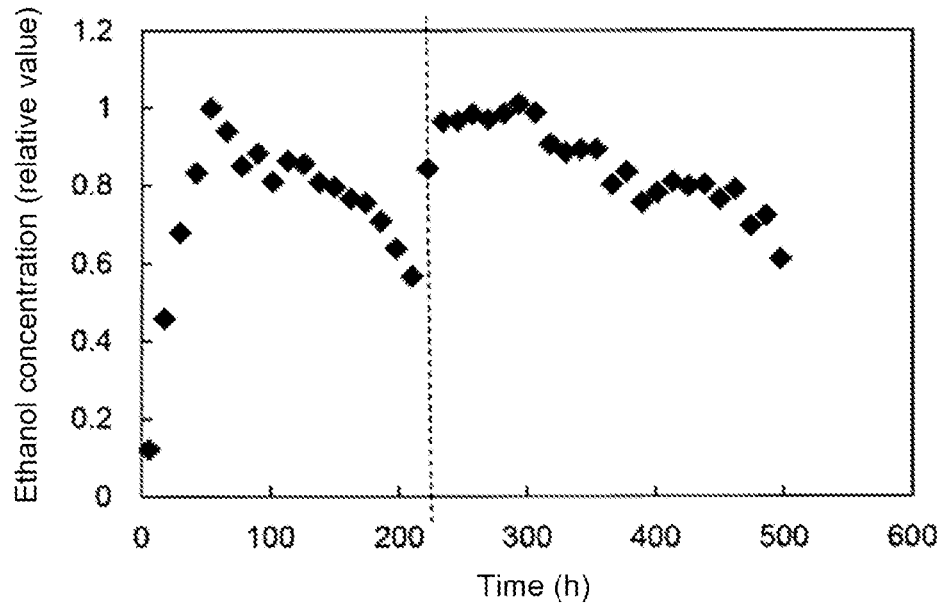

FIG. 4 shows a change in ethanol concentration (relative value) of a first reaction tank with time of Comparative Example 2. The dotted line indicates a point in time of starting the addition of an additional saccharification enzyme.

Figure 5:
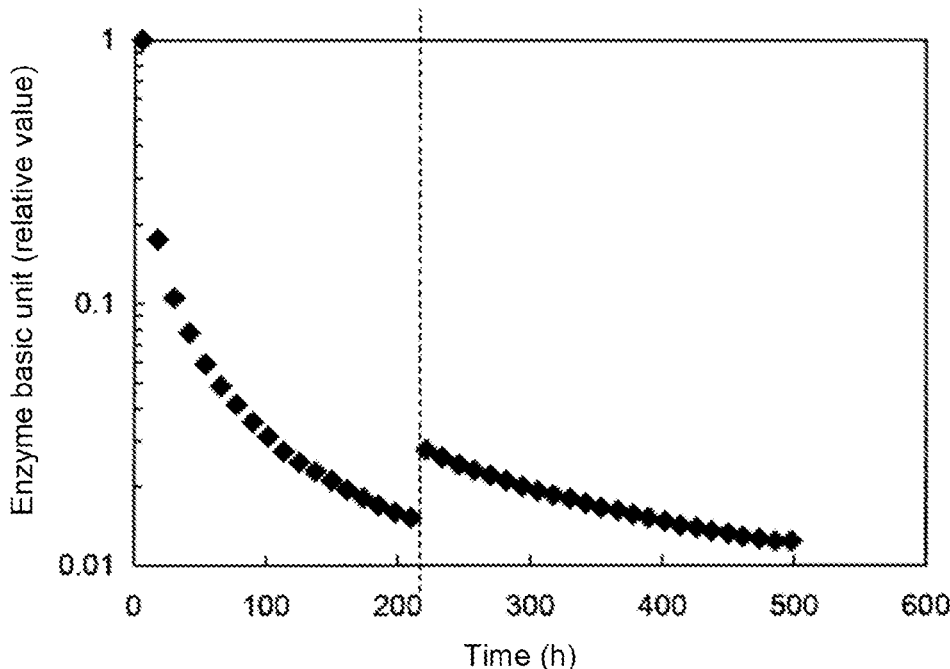

FIG. 5 shows a change in enzyme basic unit (relative value) of a first reaction tank with time of Comparative Example 2. The dotted line indicates a point in time of starting the addition of an additional saccharification enzyme.

Figure 6:
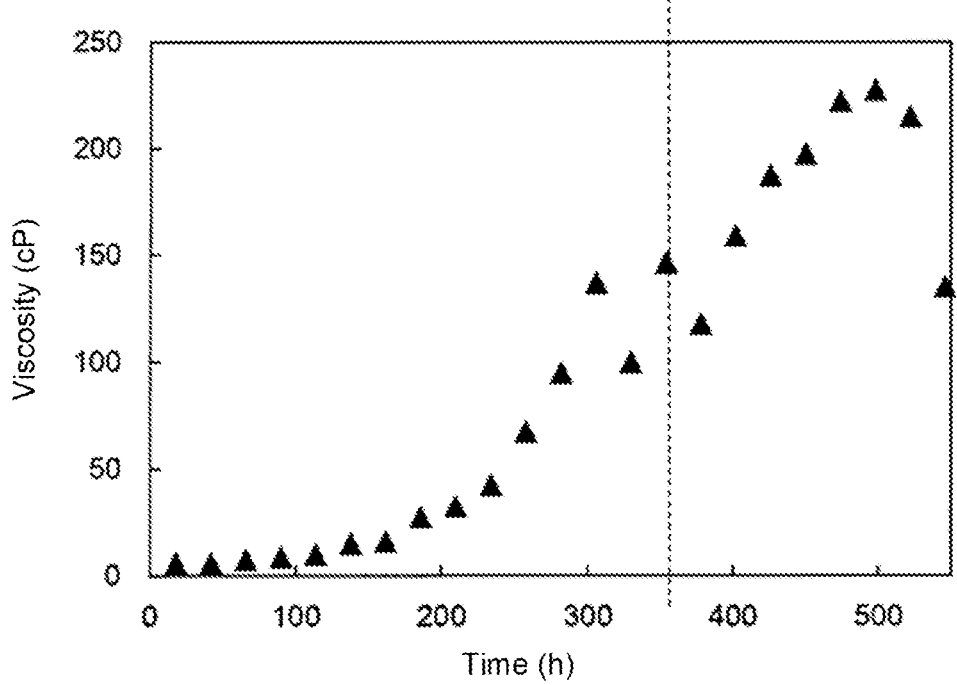

FIG. 6 shows a change in viscosity of a first reaction tank with time of Example 2. The dotted line indicates a point in time of starting the addition of an additional saccharification enzyme.

Figure 7:
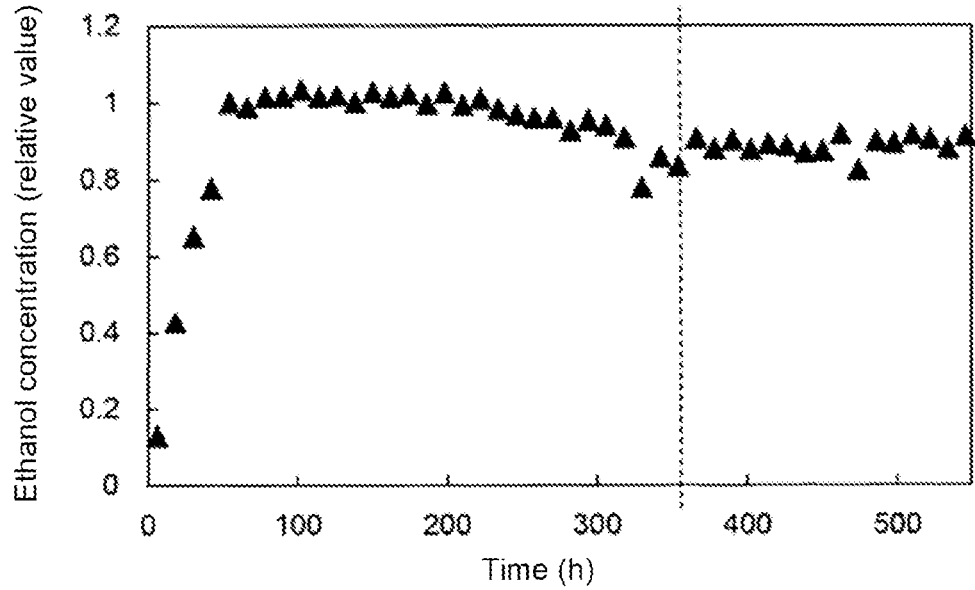

FIG. 7 shows a change in ethanol concentration (relative value) of a first reaction tank with time of Example 2. The dotted line indicates a point in time of starting the addition of an additional saccharification enzyme.

Figure 8:
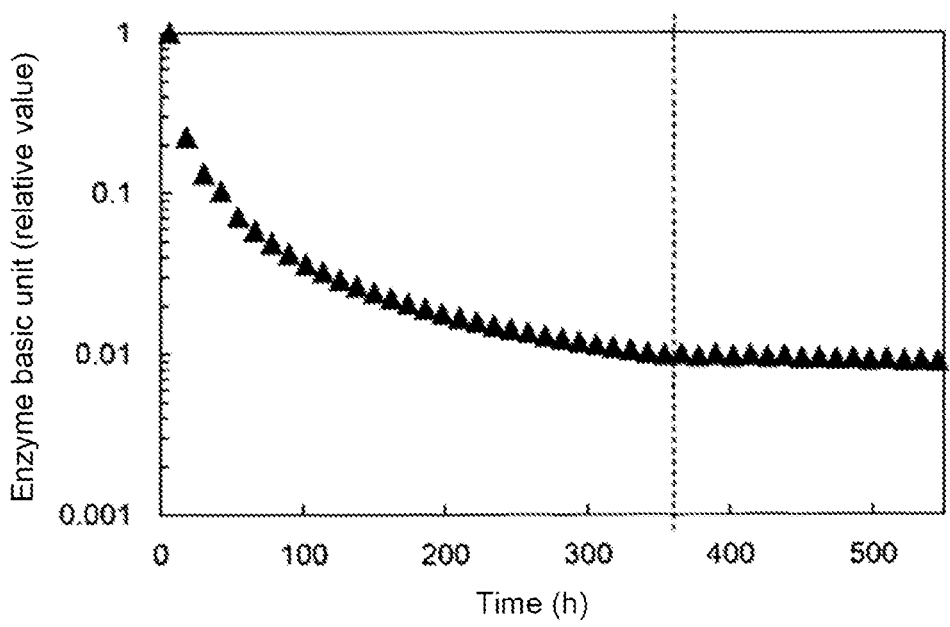

FIG. 8 shows a change in enzyme basic unit (relative value) of a first reaction tank with time of Example 2. The dotted line indicates a point in time of starting the addition of an additional saccharification enzyme.

Figure 9:
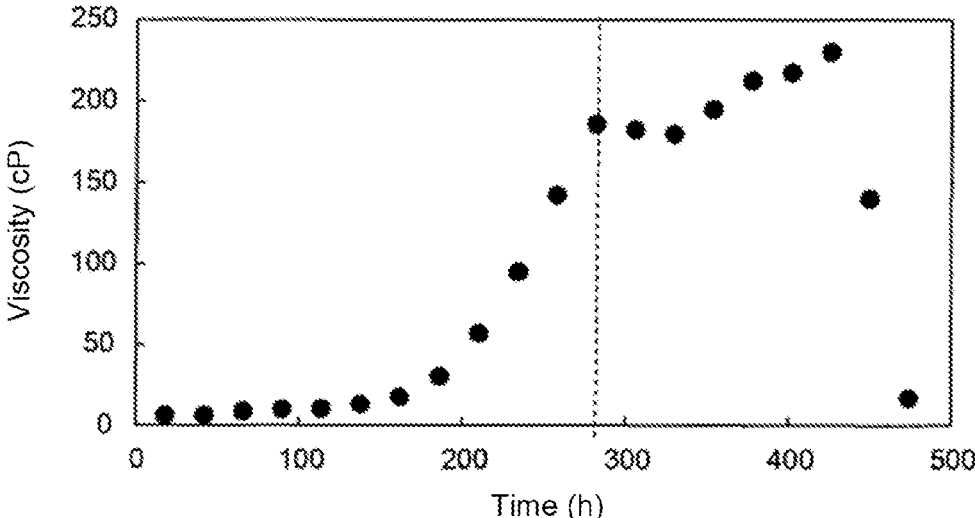

FIG. 9 shows a change in viscosity of a first reaction tank with time of Example 3. The dotted line indicates a point in time of starting the addition of an additional saccharification enzyme.

Figure 10:
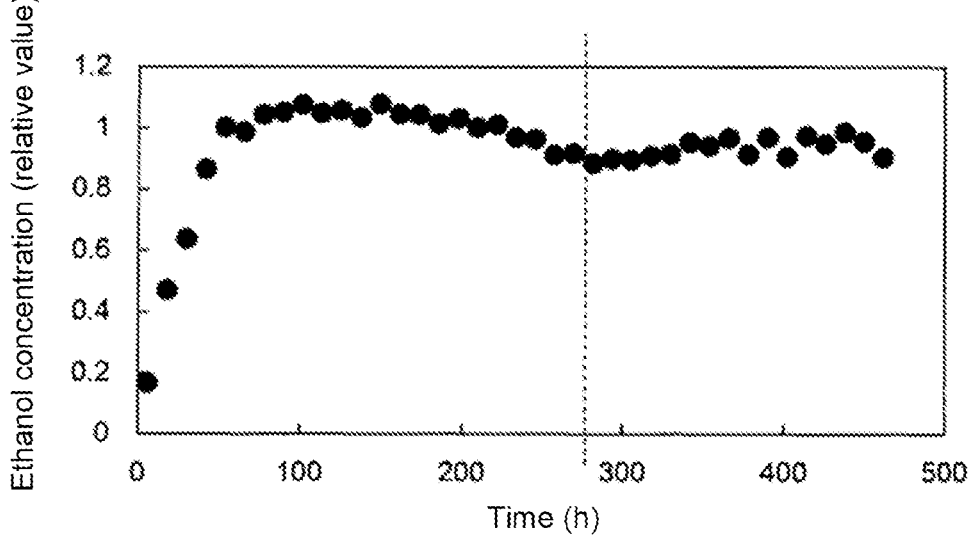

FIG. 10 shows a change in ethanol concentration (relative value) of a first reaction tank with time of Example 3. The dotted line indicates a point in time of starting the addition of an additional saccharification enzyme.

Figure 11:
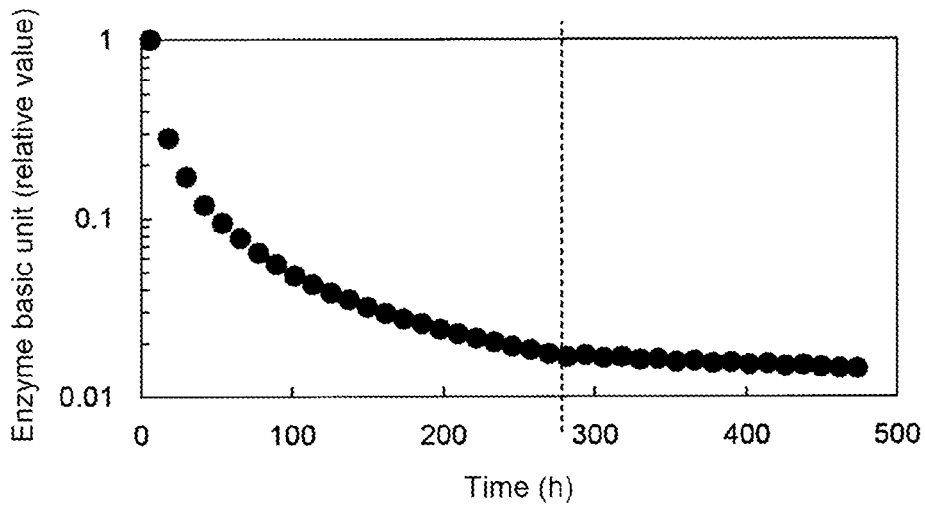

FIG. 11 shows a change in enzyme basic unit (relative value) of a first reaction tank with time of Example 3. The dotted line indicates a point in time of starting the addition of an additional saccharification enzyme.

DETAILED DESCRIPTION OF THE INVENTION

The method for producing ethanol from a lignocellulosic raw material of the present invention is characterized by comprising a step of performing multiple parallel fermentation while continuously or intermittently adding an additional saccharification enzyme to a fermentation liquid comprising a lignocellulosic raw material, a saccharification enzyme and a yeast so that the physical property value of the fermentation liquid itself is maintained within a preset range.

<Production Method>

The method for producing ethanol from a lignocellulosic raw material of the present invention comprises a step of performing multiple parallel fermentation while continuously or intermittently adding an additional saccharification enzyme to fermentation liquid comprising a lignocellulosic raw material, a saccharification enzyme and a yeast so that the physical property value of the fermentation liquid itself is maintained within a preset range.

The method for producing ethanol from a lignocellulosic raw material of the present invention may include the following steps:

(1) a multiple parallel fermentation step of allowing the above saccharification enzymes to coexist with ethanol-fermenting microorganisms, and simultaneously performing an enzymatic saccharification reaction and ethanol fermentation (2) a solid-liquid separation step (3) an ethanol concentration step (4) a solid content removal step.

<Multiple Parallel Fermentation Step>

First, a lignocellulosic raw material, a saccharification enzyme and a yeast are fed into a reaction tank. In the present invention, the lignocellulosic raw material, the saccharification enzyme and the yeast may be mixed in advance and then fed into the reaction tank, or each may be separately fed into the reaction tank. However, it is preferable to add the saccharification enzyme and the yeast to the lignocellulosic raw material fed in advance into the reaction tank. The lignocellulosic raw material is saccharified by the saccharification enzyme and the saccharides produced are converted into ethanol by fermentation with the yeast.

(Lignocellulosic Raw Material)

The lignocellulosic raw material is pulp or a raw material containing lignocellulose other than the pulp. The lignocellulosic raw material may be used alone, or a mixture of two or more thereof may be used.

Examples of the pulp include wood pulps obtained from softwood, hardwood, forest residue, construction waste, etc.; non-wood pulps such as cotton linter, cotton lint, hemp, straw and bagasse; recycled pulps made from used paper; and deinked pulps. The method for manufacturing pulp is preferably a method of highly removing lignin such as a chemical pulp manufacturing method, for example, alkali extraction or alkali cooking. Of the pulps manufactured by the chemical pulp manufacturing method, papermaking pulp is preferable in view of availability. Examples of the papermaking pulp include hardwood kraft pulps (e.g., leaf bleached kraft pulp (LBKP), leaf unbleached kraft pulp (LUKP), leaf oxygen bleached kraft pulp (LOKP)); softwood kraft pulps (e.g., needle bleached kraft pulp (NBKP), needle unbleached kraft pulp (NUKP), needle oxygen bleached kraft pulp (NOKP)); chemical pulps such as sulfite pulp (SP) and soda pulp (AP); and semichemical pulps such as semichemical pulp (SCP) and chemiground wood pulp (CGP). The pulp is preferably hardwood kraft pulp, softwood kraft pulp, sulfite pulp (SP) or semichemical pulp (SCP), and more preferably leaf bleached kraft pulp (LBKP) or needle oxygen bleached kraft pulp (NOKP).

Examples of the lignocellulosic raw material other than the pulp, as a wood-based, include chips or barks generated from papermaking trees, forest residue and thinned wood; sprouts generated from stumps of woody plants; sawdust or sawdust generated from sawmills; and pruned branches and leaves of street trees and construction waste. It is possible to use, as the wood-based lignocellulosic raw material, plants of the genus *eucalyptus* (*Eucalyptus*), plants of the genus *salix* (*Salix*), plants of the genus poplar, plants of the genus *acacia* (*Acacia*), plants of the genus *cryptomeria* (*Cryptomeria*) and the like. Of these, plants of the genus *Eucalyptus*, plants of the genus *Acacia* and plants of the genus *Salix* are preferable because they are easy to collect in large amounts as raw materials. Examples of the herbaceous raw material include agricultural wastes such as kenaf, rice straw, straw, corn cob and bagasse; residues and wastes of industrial crops such as oil crops and rubber (for example, empty fruit bunch (EFB)); and herbaceous energy crops such as *erianthus, miscanthus* and *napier* grass.

The lignocellulosic raw material other than the pulp may be biomass. Examples of the biomass include wood-derived paper, used paper, pulp sludge, sludge, sewage sludge, food waste and the like. These biomasses can be used alone, or a plurality thereof can be used in combination. The biomass may be either a dry solid, a moisture-containing solid, or a slurry.

The lignocellulosic raw materials other than the above-mentioned pulp are preferably used after subjected to a pretreatment (delignin treatment, etc.).

The concentration of the lignocellulosic raw material in the fermentation liquid in the reaction tank is preferably 5 to 30% by mass, and more preferably 10 to 20% by mass. Setting the concentration of the lignocellulosic raw material at 5% by mass or more is advantageous in avoiding a problem that the concentration of the product is finally too low, leading to an increase in cost of the concentration of ethanol. Setting the concentration of the lignocellulosic raw material at 30% by mass or less is advantageous in avoiding a problem that it becomes difficult to stir the raw material as the concentration increases, leading to low productivity.

(Saccharification Enzyme)

The saccharification enzyme is not particularly limited as long as it is a cellulolytic or hemicellulolytic enzyme. Examples of the cellulolytic enzyme include so-called cellulase, which has cellobiohydrolase activity, endoglucanase activity, beta-glucosidase activity and the like.

Each cellulolytic enzyme may be added in an appropriate amount of an enzyme having each activity. Since most of the commercially available cellulolytic enzyme agent has the above-mentioned various cellulase activities as well as hemicellulase activity, the commercially available cellulolytic enzyme agent may be used.

Examples of commercially available cellulolytic enzyme agent include cellulolytic enzyme agents derived from the genus *Trichoderma* (*Trichoderma*), the genus *Acremonium* (*Acremonium*), the genus *Aspergillus* (*Aspergillus*), the genus *Phanerochaete* (*Phanerochaete*), the genus *Trametes* (*Trametes*), the genus *Humicola* (*Humicola*), the genus *Bacillus* (*Bacillus*), the genus *Irpex* (*Irpex*) and the like. Examples of commercial products of such cellulolytic enzyme agent include cellulase CELL LEUCINE T2™ (manufactured by HPI Co., Ltd.), NOVOZYME 188™ (manufactured by Novozymes A/S), MULTIFECT CX10L™ (manufactured by Genencor International, Inc.) and GC220™ (manufactured by Genencor International, Inc.).

The saccharification enzyme used can be used alone or in combination in consideration of the properties of the cellulolytic enzyme agent. In the present invention, there are two types of enzymes: a saccharification enzyme added at the initial stage of multiple parallel fermentation and an additional saccharification enzyme added continuously or intermittently after a certain period of time. However, types of these saccharification enzymes may be the same or different.

The activity of the saccharification enzyme in the present invention is defined as follows.

A reaction was performed at 33° C. for 4 hours in a total of 10 mL system in which 375 μL of an enzyme solution and 0.5 g of leaf bleached kraft pulp (LBKP) were added to 8 mL of an aqueous solution (pH 4.8) containing 1.5 mL of 1 M acetate buffer. Thereafter, the reaction was stopped by heating at 95° C. for 10 minutes. This reaction product is analyzed by high performance liquid chromatography (HPLC) (Prominence, manufactured by Shimadzu Corporation) using a differential refractive index (RI) detector, and the glucose concentration is measured. Based on the measurement results, the amount of enzyme protein that produces 1 μmol of glucose per minute is defined as 1 unit (U).

The measurement conditions for HPLC are as follows.

Column: 80 SHODEX™ SUGAR SP0810 (manufactured by Showa Denko K.K.)

Mobile phase: Ultrapure water

Flow rate: 0.8 mL/min

Temperature: 80° C.

The initial content of the saccharification enzyme in the fermentation liquid in the reaction tank is not particularly limited and is preferably 50 to 500 U/L, and more preferably 100 to 300 U/L.

The ratio of the initial content of the saccharification enzyme to the initial content of the lignocellulosic raw material in the fermentation liquid in the reaction tank (initial content (U) of the saccharification enzyme/initial content (kg) of the lignocellulosic raw material) is preferably 500 to 50,000 U/kg, and more preferably 1,000 to 30,000 U/kg.

(Yeast)

Yeast is not particularly limited and is preferably capable of fermenting saccharides (hexose, pentose). Specifically, examples of the yeast include yeasts of the genus *Saccharomyces* such as *Saccharomyces cerevisiae* (*Saccharomyces cerevisiae*), yeasts of the genus *Pichia* such as *Pichia stipitis* (*Pichia stipitis*), yeasts of the genus *Candida* such as *Candida* shihatae (*Candida* shihatae), yeasts of the genus *Pachysolen* such as *Pachysolen tannophilus* (*Pachysolen tannophilus*), and yeasts of the genus Isachenkia such as Issatchenkia *orientalis* (Issatchenkia *orientalis*). Of these, yeasts belonging to the genus *Saccharomyces* and the genus Issatchenkia are preferable, and *Saccharomyces cerevisiae* and Issatchenkia *orientalis* are more preferable. It is also possible to use a genetically modified yeast prepared by using genetic recombination technology. It is possible to use, as the genetically modified yeast, a yeast capable of simultaneously fermenting hexose and pentose without particular limitation.

It is preferable to use yeast culture liquid as the yeast used in the multiple parallel fermentation step. Such yeast culture liquid can be obtained by culturing in a stepwise manner using culture tanks with different sizes so that the addition amount is suitable for the above step. For example, first, culture is performed in the amount of 100 to 300 mL, then culture is performed in the amount of 10 to 30 L using the obtained culture liquid, and then culture is performed in the amount of 500 to 1,000 L using the thus obtained culture liquid, and the culture liquid thus obtained can be used in the multiple parallel fermentation step.

The pH of the fermentation liquid in the reaction tank in the multiple parallel fermentation step is not particularly limited and is preferably maintained in a range of 3 to 10, and more preferably 4 to 8.

The temperature of the fermentation liquid in the reaction tank in the multiple parallel fermentation step is not particularly limited as long as it is within the optimum temperature range of the saccharification enzyme and/or the yeast and is preferably 20 to 40° C., and more preferably 30 to 40° C.

The number of bacterial cells in the reaction tank in the multiple parallel fermentation step is not particularly limited, and is preferably $10^7$ cells/mL or more, and more preferably $10^8$ cells/mL or more. The range of the number of bacterial cells is preferably $10^7$ to $10^9$ cells/mL, and more preferably $10^8$ to $10^9$ cells/mL.

The rate of increase of the solid content (suspended solid (SS)) of the fermentation liquid in the multiple parallel fermentation step is not particularly limited, and may be in a range of −1 to 5 kg/h, and preferably 0 to 5 kg/h. Here, SS refers to a suspended solid existing in the fermentation liquid.

The glucose concentration in the multiple parallel fermentation step is not particularly limited, and may be in a range of 0 to 0.2 mass/volume %.

The multiple parallel fermentation step is preferably a continuous system and may be either a semi-batch system or a batch system. Here, the continuous system refers to, for example, an embodiment in which the feeding of raw materials and the production of ethanol are continued. The reaction time varies according to the enzyme concentration and is preferably 12 to 240 hours, and more preferably 24 to 120 hours, in the case of the batch system. In the case of the semi-batch system and the continuous system, the average retention time is preferably 12 to 240 hours, and more preferably 24 to 120 hours. Here, the average retention time refers to an average retention time that the lignocellulosic raw material remains in the reaction tank from the time it is fed into the reaction tank to the time it is transferred out of the reaction tank.

The present invention includes, in the multiple parallel fermentation step, continuously or intermittently adding an additional saccharification enzyme to fermentation liquid comprising a lignocellulosic raw material, a saccharification enzyme and a yeast so that the physical property value of the fermentation liquid itself is maintained within a preset range. The physical property value is not particularly limited, and is preferably the ethanol concentration and/or the viscosity of the fermentation liquid from the viewpoint of maintaining the required enzyme amount per ethanol production amount at a constant level.

When the physical property value of the fermentation liquid is the ethanol concentration, it is preferable to add an additional saccharification enzyme so that the ethanol concentration (relative value) of the fermentation liquid is maintained at 80% or more relative to the ethanol concentration at a time of becoming a steady state after the start of fermentation. The ethanol concentration is more preferably 85% or more. The point in time of measurement of the ethanol concentration is not particularly limited and is appropriately, for example, 300 to 500 hours after the start of fermentation. The ethanol concentration of the fermentation liquid can be measured by sampling at least 1 mL of the fermentation liquid from the reaction tank, stopping the reaction, and then analyzing the supernatant by HPLC. Such measurement can be easily performed by using Prominence (Shimadzu Corporation).

Here, the above-mentioned "point in time of becoming a steady state after the start of fermentation" is a point in time when the ethanol concentration first reaches the maximum value after the start of fermentation, and preferably means a point in time that the fluctuation range of the ethanol concentration remains less than 20% thereafter. It is possible to appropriately change a point in time of becoming a steady state after the start of fermentation according to the reaction conditions and the like. For example, the point in time is 12 to 240 hours, and preferably 24 to 120 hours, after the start of fermentation.

According to one embodiment of the present invention, the amount of the additional saccharification enzyme to be added is preferably such that the enzyme basic unit (U/L) in the fermentation liquid is maintained at 0.1 to 30% as a relative value to the enzyme basic unit, for example, after 1 to 12 hours, and preferably 1 to 8 hours, from the start of fermentation. Here, the enzyme basic unit refers to the amount of enzyme required to produce a unit volume of ethanol. The enzyme basic unit is used as an index of enzyme cost, and can be preferably calculated from the following formula.

Enzyme basic unit (U/L)=total amount (U) of sac-
charification enzyme/total amount (U) of etha-
nol produced (L)

From the viewpoint of suppressing the enzyme cost, it is particularly advantageous in that efficient ethanol production is possible to perform an enzyme reaction so that the enzyme basic unit is continuously reduced. The amount of the additional saccharification enzyme is preferably set so that the enzyme basic unit (relative amount) of the fermentation liquid becomes, for example, 0.1 to 30%, preferably 0.1 to 10%, and more preferably 0.1 to 2%, relative to the enzyme basic unit after 1 to 12 hours from the start of fermentation. The point in time of calculation of the enzyme basic unit is not particularly limited and is appropriately set at, for example, 300 to 500 hours.

The amount of the additional saccharification enzyme to be added can be set at, for example, 20 U or less, preferably 1 U or more and 15 U or less, and more preferably 3 U or more and 10 U or less, per 1 L of the fermentation liquid. Here, the amount of the additional saccharification enzyme to be added can be calculated as the addition amount of the additional saccharification enzyme to be added per day. Further, the amount of the additional saccharification enzyme can be appropriately set according to the temperature, pH, time, the properties and combinations of the enzymes and the like of the multiple parallel fermentation step.

The mass ratio of the addition amount of the additional saccharification enzyme per day to the initial content of the saccharification enzyme in the fermentation liquid (the addition amount of the additional saccharification enzyme per day:the initial content of saccharification enzyme in the fermentation liquid) is not particularly limited, and is preferably 1:10 to 1:100, more preferably 1:15 to 1:80, and still more preferably 1:15 to 1:50.

The addition of the additional saccharification enzyme is performed continuously or intermittently. Here, when the addition of the additional saccharification enzyme is performed intermittently, the addition of the additional saccharification enzyme is preferably every 2 to 192 hours, more preferably every 6 to 96 hours, and still more preferably every 12 to 48 hours.

It is preferable to start the addition of the additional saccharification enzyme so that the physical property value of the fermentation liquid itself is measured and the measured value is maintained within a preset range.

The viscosity of the fermentation liquid can also be used as an index for adding the additional saccharification enzyme. The viscosity may be thought to use as an index regarding the degree of progress of saccharification of the lignocellulosic raw material. When the physical property value of the fermentation liquid is the viscosity of the fermentation liquid, the viscosity can be appropriately determined according to the stirring conditions, reaction conditions and the like. However, when the viscosity exceeds 140 cP, the additional saccharification enzyme is preferably added to the fermentation liquid. The viscosity index can be used particularly advantageously when the reaction in the multiple parallel fermentation step is a continuous system. When the multiple parallel fermentation step is a semi-batch system or a batch system, the viscosity of the fermentation liquid can be appropriately determined according to the stirring conditions, reaction conditions and the like. However, when the viscosity exceeds 4 cP, the additional saccharification enzyme is preferably added to the fermentation liquid.

When the physical property value of the fermentation liquid is the viscosity, the viscosity can be appropriately determined according to the stirring conditions, reaction conditions and the like. However, the above-mentioned preset range is preferably 300 cP or less as the viscosity of the fermentation liquid. The viscosity is more preferably 250 cP or less. The viscosity range can be advantageously used when the reaction in the multiple parallel fermentation step is a continuous system. When the reaction in the multiple parallel fermentation step is a semi-batch system or a batch system, it is preferable to add an additional saccharification enzyme to the fermentation liquid so that the viscosity of the fermentation liquid is 20 cP or less.

The viscosity of the fermentation liquid can be measured by sampling at least 10 mL of the fermentation liquid from the reaction tank and directly subjecting it to the viscosity measurement with a viscometer. Such measurement can be easily performed by using a viscometer (Analog B-type Viscometer LV-T, BROOKFIELD). The measurement of the viscosity is performed at a temperature of 25° C.

In the multiple parallel fermentation step, it is preferable to adjust the concentration of the lignocellulosic raw material in the fermentation liquid so as to be maintained within a predetermined range. The predetermined range is 5 to 30% by mass, and preferably 10 to 20% by mass. The adjustment is performed, for example, by feeding a lignocellulosic raw material to the reaction tank. Here, the feeding rate of the lignocellulosic raw material to the reaction tank is not particularly limited. However, when the multiple parallel fermentation step is a continuous system and the fermentation liquid is discharged from the reaction tank, it is preferable that the feeding rate of the lignocellulosic raw material to the reaction tank and the discharge rate of the fermentation liquid from the reaction tank are on the same level. As shown below, in the solid-liquid separation step, when the solid content concentrated fermentation liquid is recovered after separation of the aqueous ethanol solution and then transferred to the reaction tank, it is preferable that the total feeding rate of the solid content concentration fermentation liquid and the lignocellulosic raw material to the reaction tank and the discharge rate of the fermentation liquid from the reaction tank are on the same level.

According to one embodiment of the present invention, from the viewpoint of yeast growth or from the viewpoint of preventing the risk of raw materials being transferred from the reaction tank in an unreacted state, the reaction tanks in which multiple parallel fermentation is performed are at least two tanks connected to each other. It is preferable that at least two reaction tanks are connected in series. In such embodiment, for example, the respective reaction tanks can be connected in series so that first fermentation liquid discharged from a first reaction tank is injected into a second reaction tank through a line part.

Here, it is preferable that the first reaction tank stores the fermentation liquid and continuously feeds the additional lignocellulosic raw material. The feeding amount of the lignocellulosic raw material is preferably adjusted so that the concentration of the lignocellulosic raw material in the fermentation liquid in the first reaction tank is maintained within a predetermined range, and the above-mentioned predetermined range is 5 to 30% by mass, and preferably 10 to 20% by mass.

Further, it is preferable that the fermentation liquid in the second reaction tank is one in which a part of the fermentation liquid is continuously transferred from the first reaction tank.

When at least two tanks connected to each other are used as the reaction tanks for multiple parallel fermentation, the physical property value of the fermentation liquid that is an index of the addition of the additional saccharification enzyme preferably uses the physical property value of the fermentation liquid in the first reaction tank. The fermentation liquid in the first reaction tank has a large proportion of the unreacted lignocellulose raw material, and a decrease in enzyme activity tends to affect the physical property value, which is advantageous in using it as an accurate index for the addition of additional saccharification enzyme. Therefore, the additional saccharification enzyme is preferably added to the first reaction tank.

<Solid-Liquid Separation Step>

The fermentation liquid discharged from the reaction tank can be separated into a solid content concentrated fermentation liquid and an aqueous solution, for example, a solid content concentrated fermentation liquid and an aqueous ethanol solution, by a separation apparatus such as a vacuum distillation apparatus or a membrane separation apparatus in the solid-liquid separation step. When the reaction tanks are two tanks, it is preferable that the fermentation liquid is discharged from the second reaction tank and then transferred to an ethanol separator. It is possible to use, as the vacuum distillation apparatus, a rotary evaporator, a flash evaporator or the like. Since ethanol can be separated at a low temperature under reduced pressure, inactivation of the enzyme can be prevented. The thus obtained aqueous ethanol solution can be concentrated in the following ethanol concentration step.

The solid content concentrated fermentation liquid may be recovered after separating the aqueous ethanol solution and then transferred to the reaction tank as it is, or may be separated into a residue and a supernatant by a solid content removing device as shown below. When the reaction tanks are at least two tanks, the reaction tank to be transferred is preferably a first reaction tank.

<Ethanol Concentration Step>

The aqueous ethanol solution obtained in the solid-liquid separation step can be further concentrated by a distillation treatment or various separation membranes, for example, a zeolite membrane, thus enabling the production of high-purity ethanol. The aqueous ethanol solution may be transferred to the reaction tank after removing the ethanol.

<Solid Content Removing Step>

The solid content concentrated fermentation liquid after separating the aqueous ethanol solution in the solid-liquid separation step may be transferred to a solid content removing device and then separated into a residue and a supernatant. The thus obtained supernatant may be transferred to a reaction tank. When the tanks are at least two tanks, the reaction tank be transferred is preferably a first reaction tank. It is possible to use, as the solid content removing device, a disc type centrifuge, a screw press, a screen, a filter press, a belt press, a rotary press and the like. The separated residue contains an enzyme, lignin and a yeast. The enzyme adsorbed on the residue can be isolated, recovered and reused. Lignin can also be recovered as a combustion raw material and used as energy, or lignin can also be recovered and effectively used. The yeast can also be separated from the residue and reused in the multiple parallel fermentation step.

According to the method for producing ethanol of the present invention, ethanol can be efficiently produced from a lignocellulosic raw material. The ethanol obtained by the method for producing ethanol can be suitably used as, for example, ethanol for fuel, ethanol for industrial use, ethanol for food additives, and the like.

EXAMPLES

The present invention will be described in more detail by way of the following Examples, but the present invention is not limited thereto. Unless otherwise specified, the units and measurement methods described in the present specification are based on the Japanese Industrial Standards (JIS).

Viscosity Measurement Method

The viscosity of each fermentation liquid obtained in the respective Examples and Comparative Examples was measured by using a viscometer (Analog B-type viscometer LV-T, BROOKFIELD). The measurement was performed using Spindle No. 27 at a rotation speed of 60 rpm and a temperature of 25° C.

Turbidity Measurement Method

The SS turbidity of each fermentation liquid obtained in the respective Examples and Comparative Examples was measured using a turbidity meter (portable turbidity meter 2100Q, HACH). Then, a difference between the thus obtained SS turbidity and the SS turbidity measured before 12 hours was determined, and the SS increase rate was calculated by dividing by 12 hours, which is the elapsed time between two points.

Method for Measuring Number of Cells

The number of bacterial cells in each culture liquid and each fermentation liquid obtained in the respective Examples and Comparative Examples was observed and measured with an optical microscope (magnification of 400 times) using a Thoma hemocytometer.

Method for Measuring Glucose and Ethanol Concentrations

Regarding the glucose concentration and the ethanol concentration in the fermentation liquid, the fermentation liquid was heated at 95° C. for 10 minutes to inactivate a yeast and an enzyme, and then analysis and measurement were performed by HPLC (Prominence, manufactured by Shimadzu Corporation) using a differential refractometer (RI) detector.

The measurement conditions for HPLC are as follows.

Column: 80SHODEX™ SUGAR SP0810 (manufactured by Showa Denko K.K.)

Mobile phase: Ultrapure water

Flow rate: 0.8 mL/min

Temperature: 80° C.

Calculation Method of Enzyme Basic Unit

Regarding the enzyme basic unit from the start of multiple parallel fermentation in the respective Examples and Comparative Examples to a predetermined time, the enzyme basic unit (U/L) was calculated by the following calculation formula based on the ethanol concentration contained in the fermentation liquid obtained in respective Examples and Comparative Examples.

Enzyme basic unit (U/L)=total amount (U) of saccharification enzyme/total amount (L) of ethanol produced The enzyme basic unit is an index of enzyme cost and indicates the amount of an enzyme required to produce a unit capacity of ethanol.

Example 1: Test in 5 L Reaction Tank (with Repeated Addition of a Small Amount of Additional Saccharification Enzyme)

In a 500 mL flask, 200 mL of an aqueous solution of 1% by mass/volume of CSL (corn steep liquor) and 2% by mass/volume of glucose was prepared. Yeast *Saccharomyces cerevisiae* was inoculated into the thus obtained aqueous solution at a concentration of $1 \times 10^7$ cells/mL and cultured overnight to prepare yeast culture liquid.

Next, a multiple parallel fermentation test was performed. In a 5 L reaction tank, 300 g (total dry weight) of needle oxygen bleached kraft pulp (NOKP), 6.6 g of urea, 395 U of a saccharification enzyme and yeast culture liquid having a final concentration of $1.0 \times 10^7$ cells/mL were added and the amount of the liquid was adjusted with sterile water so that the total volume became 3 L. The pH was adjusted to 4.8 with 5N sulfuric acid and an aqueous 5N sodium hydroxide solution. The culture tank was controlled to be constant at a temperature of 33° C., a stirring rate of 206 rpm and pH of 4.8. After 48 hours, half of the fermentation liquid was extracted once every 24 hours and centrifuged with a centrifuge (KUBOTA™ 5500 Tabletop Refrigerated Centrifuge), and then ethanol was removed from the thus obtained supernatant using an evaporator (Nihon BUCHI K.K., ROTOVAPOR™ R-300). Both the supernatant from which ethanol had been removed and the solid recovered by centrifugation were returned to the reaction tank. At this time, NOKP having an absolute dry weight of 150 g, which corresponds to half of the initial addition amount, was also added to the fermentation liquid.

The conditions of the multiple parallel fermentation step are shown below.

TABLE 1

| Item | Value |
| --- | --- |
| Dry pulp concentration, % (w/w) | 10 |
| Temperature, ° C. | 33 |
| Enzyme initial addition amount, U | 395 |
| pH | 4.8 |
| System capacity, L | 3 |
| Retention time, hours | 48 |

From a point in time of 168 hours after the start of the reaction under the above conditions, 22 U of an additional saccharification enzyme was added once every 24 hours.

The fermentation liquid was sampled once every 24 hours, followed by measurement of the viscosity, the ethanol concentration and the glucose concentration, measurement of the number of bacterial cells, and further calculation of the SS increase rate.

Figure 1:
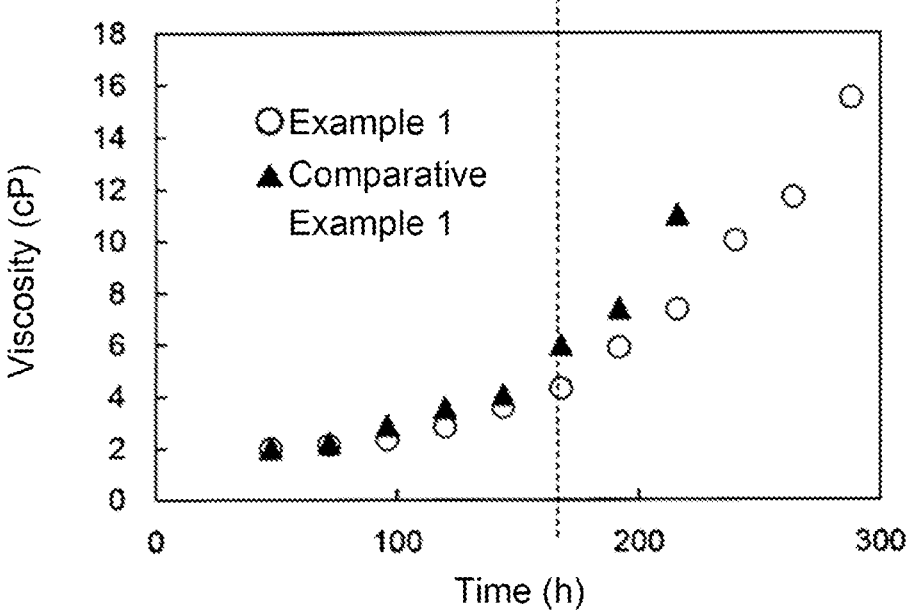
FIG. 1 shows a change in viscosity with time of Example 1 and Comparative Example 1. The dotted line indicates a point in time of starting the addition of an additional saccharification enzyme.
Figure 2:
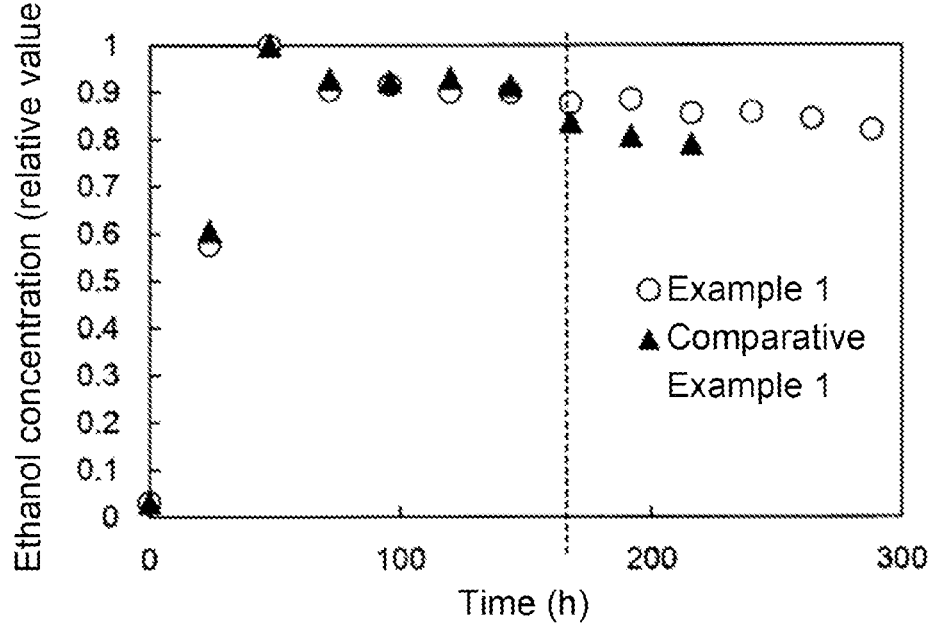
FIG. 2 shows a change in ethanol concentration (relative value) with time of Example 1 and Comparative Example 1. The dotted line indicates a point in time of starting the addition of an additional saccharification enzyme.

The measurement results of the viscosity are shown in FIG. 1, and the measurement results of the ethanol concentration (relative value) are shown in FIG. 2. In FIG. 2, the ethanol concentration at a point in time of becoming a steady state after the start of the test (48 hours after the start of the test) is set at 1.

The number of bacterial cells from the start to the end of the multiple parallel fermentation was $1 \times 10^8$ to $1 \times 10^9$ cells/mL. The SS increase rate was 0.00036 kg/h at 168 hours and 0.00057 kg/h at 288 hours. The glucose concentration was 0.023 mass/volume % at 168 hours and 0 mass/volume % at 288 hours.

Comparative Example 1: Test in 5 L Reaction Tank (without Addition of Additional Saccharification Enzyme)

A multiple parallel fermentation test was performed by the method of Example 1 except that no additional saccharification enzyme was added from a point in time of 168 hours after the start of the reaction.

The results are shown in FIGS. 1 and 2.

The number of bacterial cells from the start to the end of the multiple parallel fermentation was $1 \times 10^8$ to $1 \times 10^9$ cells/mL. The glucose concentrations were 0 mass/volume % both at 168 hours and 288 hours.

Although the ethanol concentration decreased in both the systems of Example 1 and Comparative Example 1, the system of Example 1 (with the addition of a small amount of additional saccharification enzyme) showed moderate decrease in both ethanol concentration and viscosity increasing behavior as compared with the system of Comparative Example 1 (without adding a small amount of additional saccharification enzyme), thus judging to be effective of adding a small amount of the additional saccharification enzyme.

Comparative Example 2: Test in a 12,000 L Volume Reaction Tank (with a Single Addition of Additional Saccharification Enzyme)

Yeast *Saccharomyces cerevisiae* used for fermentation was prepared in three stages of (1) 200 mL culture using a 500 mL flask, (2) 20 L culture using a 30 L culture tank, and (3) 800 L culture using a 900 L culture tank. In each stage, an aqueous solution of 1 mass/volume % of CSL and 2 mass/volume % of glucose was prepared, inoculated at a concentration of $1 \times 10^7$ cells/mL and cultured for 12 hours to prepare yeast culture liquid.

Next, a multiple parallel fermentation test was performed. A first reaction tank having a maximum capacity of 12,000 L was filled with sterilized water and, after adding 12.6 kg of urea, feeding of needle oxygen bleached kraft pulp (NOKP) was started at a rate of 13.75 kg/h in terms of absolute dry weight so that the dry pulp concentration became 10% (w/w) at a point in time of elapsing 48 hours of the retention time. After adjusting the pH to 4.8 by adding 3N sulfuric acid and an aqueous 3N sodium hydroxide solution, 878,735 U of a saccharification enzyme and the entire amount of the yeast culture liquid prepared in the 900 L culture tank were added to initiate the reaction. The reaction tank was controlled to be constant at a temperature of 33° C., a stirring rate of 24 rpm and pH of 4.8. At a point in time of elapsing 48 hours, half the amount of the first reaction tank was transferred to a second reaction tank having a maximum of 10,000 L. After completion of the transfer to the second reaction tank, the transfer of the fermentation liquid was started from the second reaction tank to a vacuum distillation column at a rate of 140 kg/h, and then the operations of distilling off an aqueous ethanol solution at a rate of 45 kg/h and collecting a solid content concentrated fermentation liquid into the first reaction tank at a rate of 95 kg/h were continued until the operation was stopped. During this period, the feeding to the NOKP first reaction tank was continued at a constant speed (45 kg/h).

The conditions of the multiple parallel fermentation step are shown below.

TABLE 2

| Item | Value |
| --- | --- |
| Dry pulp concentration, % (w/w) | 10 |
| Temperature, ° C. | 33 |
| Enzyme initial addition amount, U | 878,735 |
| pH | 4.8 |
| Total system capacity, L | 6,600 |
| Number of tanks | 2 |
| Retention time, hours | 48 |

At a point in time of 222 hours after the start of the reaction, since the ethanol concentration in the first reaction tank decreased significantly, 878,735 U of the enzyme was added again.

The fermentation liquid was first sampled after 6 hours and then sampled once every 12 hours, followed by measurement of the viscosity, the ethanol concentration and the glucose concentration, measurement of the number of bacterial cells, and further calculation of the SS increase rate.

Figure 3:
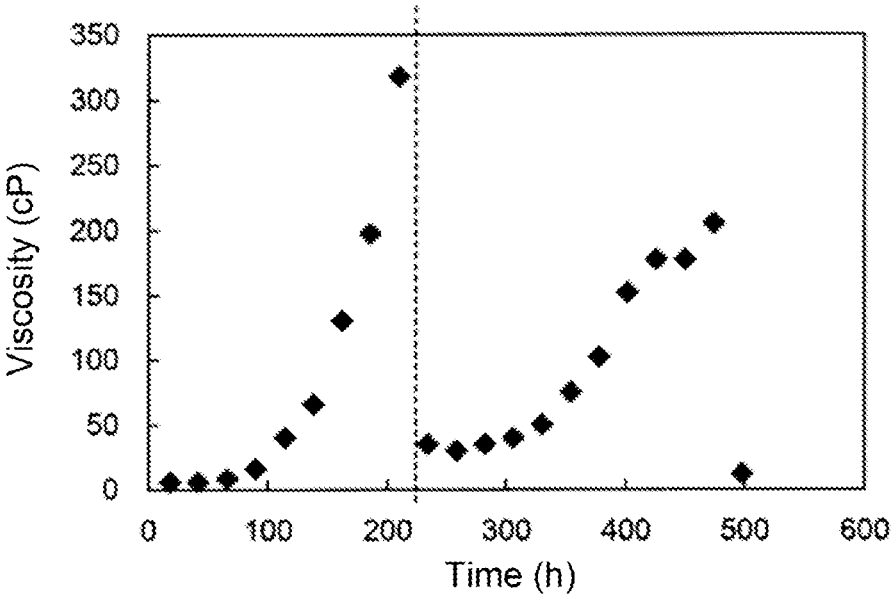
FIG. 3 shows a change in viscosity of a first reaction tank with time of Comparative Example 2. The dotted line

The results of the viscosity measurement of the first reaction tank are shown in FIG. 3, the measurement results of the ethanol concentration (relative value) of the first reaction tank are shown in FIG. 4, and the results of the enzyme basic unit (relative value) are shown in FIG. 5. In FIG. 4, the ethanol concentration at a point in time of becoming a steady state after the start of the test (54 hours after the start of the test) is set at 1. In FIG. 5, the enzyme basic unit (U/L) at 6 hours after the start of the test is set at 1.

The number of bacterial cells in the first reaction tank from the start to the end of the multiple parallel fermentation was $1 \times 10^8$ to $1 \times 10^9$ cells/mL. The SS increase rates of the first reaction tank were 0.335 kg/h at 222 hours and 0.0093 kg/h at 498 hours. The glucose concentrations were 0.142 mass/volume % at 222 hours and 0.075 mass/volume % at 498 hours.

Although 878,735 U of the enzyme was added at once, only temporary productivity improving effect was obtained. Therefore, it was found that even if a large amount was added at one time, the effect commensurate with the amount added could not be obtained.

Example 2: Test in 12,000 L Volume Reaction Tank (with Repeated Addition of a Small Amount of Additional Saccharification Enzyme)

Yeast *Saccharomyces cerevisiae* used for fermentation was prepared in three stages of (1) 200 mL culture using a 500 mL flask, (2) 20 L culture using a 30 L culture tank, and (3) 800 L culture using a 900 L culture tank. In each stage, an aqueous solution of 1 mass/volume % of CSL and 2 mass/volume % of glucose was prepared, inoculated at a concentration of $1 \times 10^7$ cells/mL and cultured for 12 hours to prepare yeast culture liquid.

Next, a multiple parallel fermentation test was performed. A first reaction tank having a maximum capacity of 12,000 L was filled with sterilized water and, after adding 14 kg of urea and 63 kg of CSL, feeding of leaf bleached kraft pulp (LBKP) was started at a rate of 15.2 kg/h in terms of absolute dry weight so that the dry pulp concentration became 10% (w/w) at a point in time of elapsing 48 hours of the retention time. After adjusting the pH to 4.8 by adding 3N sulfuric acid and an aqueous 3N sodium hydroxide solution, 966,608 U of a saccharification enzyme and the entire amount of the yeast culture liquid prepared in the 900 L culture tank were added to initiate the reaction. The reaction tank was controlled to be constant at a temperature of 33° C., a stirring rate of 24 rpm and pH of 4.8. At a point in time of elapsing 48 hours, half the amount of the first reaction tank was transferred to a second reaction tank having a maximum of 10,000 L. After completion of the transfer to the second reaction tank, the transfer of the fermentation liquid was started from the second reaction tank to a vacuum distillation apparatus at a rate of 150 kg/h, and then the operations of distilling off an aqueous ethanol solution at a rate of 40 kg/h and collecting a solid content concentrated fermentation liquid into the first reaction tank at a rate of 110 kg/h were continued until the operation was stopped. During this period, the feeding of the LBKP-containing liquid to the first reaction tank was continued at a constant speed (40 kg/h).

The conditions of the parallel double fermentation step are shown below.

TABLE 3

| Item | Value |
|---|---|
| Dry pulp concentration, % (w/w) | 10 |
| Temperature, ° C. | 33 |
| Enzyme initial addition amount, U | 966,608 |
| pH | 4.8 |
| Total system capacity, L | 7,300 |
| Number of tanks | 2 |
| Retention time, hours | 48 |

At a point in time of elapsing 354 hours after the start of the reaction, the addition of a small amount of the additional saccharification enzyme was started. The additional saccharification enzyme was added to the first reaction tank. The enzyme was added in the amount of 49,210 U every 24 hours.

The fermentation liquid was first sampled after 6 hours and then once every 12 hours, followed by measurement of the viscosity, the ethanol concentration and the glucose concentration, measurement of the number of bacterial cells, and further calculation of the SS increase rate.

The results of the viscosity measurement of the first reaction tank are shown in FIG. 6, the results of the measurement of the ethanol concentration (relative value) of the first reaction tank are shown in FIG. 7, and the results of the enzyme basic unit (relative value) are shown in FIG. 8. In FIG. 7, the ethanol concentration at a point in time of becoming a steady state after the start of the test (54 hours after the start of the test) is set at 1. In FIG. 8, the enzyme basic unit (U/L) at 6 hours after the start of the test is set at 1.

The number of bacterial cells in the first reaction tank from the start to the end of parallel double fermentation was $1 \times 10^8$ to $1 \times 10^9$ cell/mL. The SS increase rates of the first reaction tank were 0.16 kg/h at 354 hours and 0.24 kg/h at 546 hours. The glucose concentrations were 0.079 mass/volume % at 354 hours and 0.097 mass/volume % at 546 hours.

It was possible to confirm retention of the ethanol concentration and alleviation of the viscosity increase due to the repeated addition of a small amount of the additional saccharification enzyme.

Example 3: Test in 12,000 L Volume Reaction Tank (with Repeated Addition of a Small Amount of Additional Saccharification Enzyme)

Yeast *Saccharomyces cerevisiae* used for fermentation was prepared in three stages of (1) 200 mL culture using a 500 mL flask, (2) 20 L culture using a 30 L culture tank, and (3) 800 L culture using a 900 L culture tank. In each stage, an aqueous solution of 1 mass/volume % of CSL and 2 mass/volume % of glucose was prepared, inoculated at a concentration of $1 \times 10^7$ cells/mL and cultured for 12 hours to prepare yeast culture liquid.

Next, a multiple parallel fermentation test was performed. A first reaction tank having a maximum capacity of 12,000 L was filled with sterilized water and, after adding 14 kg of urea and 137 kg of CSL, feeding of leaf bleached kraft pulp (LBKP) was started at a rate of 15.2 kg/h in terms of an absolute dry weight so that the dry pulp concentration became 10% (w/w) at a point in time of elapsing 48 hours of the retention time. After adjusting the pH to 4.8 by adding 3N sulfuric acid and an aqueous 3N sodium hydroxide solution, 799,649 U of a saccharification enzyme and the entire amount of the yeast culture liquid prepared in the 900 L culture tank were added to initiate the reaction. The reaction tank was controlled to be constant at a temperature of 33° C., a stirring rate of 24 rpm and pH of 4.8. At a point in time of elapsing 48 hours, half the amount of the first reaction tank was transferred to a second reaction tank having a maximum of 10,000 L. After completion of the transfer to the second reaction tank, the transfer of the fermentation liquid was started from the second reaction tank to a vacuum distillation column at a rate of 150 kg/h, and then the operations of distilling off an aqueous ethanol solution at a rate of 40 kg/h and collecting a solid content concentrated fermentation liquid into the first reaction tank at a rate of 110 kg/h were continued until the operation was stopped. During this period, the feeding of the LBKP-containing liquid to the first reaction tank was continued at a constant speed (40 kg/h).

The conditions of the parallel double fermentation step are shown below.

TABLE 4

| Item | Value |
| --- | --- |
| Dry pulp concentration, % (w/w) | 10 |
| Temperature, ° C. | 33 |
| Enzyme initial addition amount, U | 799,649 |
| pH | 4.8 |
| Total system capacity, L | 7,300 |
| Number of tanks | 2 |
| Retention time, hours | 48 |

At a point in time of elapsing 282 hours after the start of the reaction, the addition of a small amount of the additional saccharification enzyme was started. The additional saccharification enzyme was added to the first reaction tank. The enzyme was added in the amount of 49,210 U every 24 hours.

The fermentation liquid was first sampled after 6 hours and then once every 12 hours, followed by measurement of the viscosity, the ethanol concentration and the glucose concentration, measurement of the number of bacterial cells, and further calculation of the SS increase rate.

The results of the viscosity measurement of the first reaction tank are shown in FIG. 9, the results of the measurement of the ethanol concentration (relative value) of the first reaction tank are shown in FIG. 10, and the results of the enzyme basic unit (relative value) are shown in FIG. 11. In FIG. 10, the ethanol concentration at a point in time of becoming a steady state after the start of the test (54 hours after the start of the test) is set at 1. In FIG. 11, the enzyme basic unit (U/L) at 6 hours after the start of the test is set at 1.

The number of bacterial cells in the first reaction tank from the start to the end of parallel double fermentation was $1 \times 10^8$ to $1 \times 10^9$ cell/mL. The SS increase rates of the first reaction tank were −0.31 kg/h at 282 hours and 0.83 kg/h at 474 hours. The glucose concentrations were 0.076 mass/volume % at 282 hours and 0.039 mass/volume % at 474 hours.

It was possible to confirm retention of the ethanol concentration and alleviation of the viscosity increase due to the repeated addition of a small amount of the additional saccharification enzyme.

The invention claimed is:

1. A method for producing ethanol from a lignocellulosic raw material, comprising:
   a step of performing multiple parallel fermentation with a fermentation liquid comprising a lignocellulosic raw material, an initial content of a saccharification enzyme and a yeast to produce ethanol, wherein during the multiple parallel fermentation, an additional saccharification enzyme is continuously or intermittently added to the fermentation liquid beginning at 354 hours after the start of fermentation until 500 hours after the start of fermentation while maintaining ethanol concentration in the fermentation liquid at 80% or more relative to the ethanol concentration at a time of becoming a steady state after the start of fermentation,
   a step of performing a solid-liquid separation of an aqueous ethanol solution from the fermentation liquid to produce a solid content concentrated fermentation liquid, and
   a step of transferring the solid content concentrated fermentation liquid to a reaction tank after separating the aqueous ethanol solution,
   wherein the multiple parallel fermentation step is a continuous system,
   wherein a mass ratio of the addition amount of the additional saccharification enzyme per day to the initial content of the saccharification enzyme in the fermentation liquid is 1:10 to 1:100, and
   wherein the time of becoming a steady state after the start of fermentation is a time when the ethanol concentration first reaches a maximum value after the start of fermentation and when the ethanol concentration fluctuates less than 20% thereafter.

2. The method for producing ethanol according to claim 1, wherein the additional saccharification enzyme is added so that an enzyme basic unit in the fermentation liquid is maintained at 0.1 to 30% relative to the enzyme basic unit after 1 to 12 hours from the start of fermentation.

3. The method for producing ethanol according to claim 1, wherein the additional saccharification enzyme is added to the fermentation liquid in an amount of 20 U/L or less.

4. The method for producing ethanol according to claim 1, wherein the additional saccharification enzyme is intermittently added every 2 to 192 hours.

5. The method for producing ethanol according to claim 1, wherein the concentration of the lignocellulosic raw material in the fermentation liquid is adjusted so as to be maintained within a predetermined range.

6. The method for producing ethanol according to claim 1, wherein the concentration of the lignocellulosic raw material in the fermentation liquid is adjusted so as to be maintained at 5 to 30% by mass.

7. The method for producing ethanol according to claim 1, wherein the multiple parallel fermentation is performed in at least two reaction tanks connected to each other.

8. The method for producing ethanol according to claim 7, wherein the at least two reaction tanks are connected in series.

9. The method for producing ethanol according to claim 7, wherein the at least two reaction tanks comprise a first reaction tank which stores the fermentation liquid and in which additional lignocellulosic raw material is continuously fed.

10. The method for producing ethanol according to claim 7, wherein the at least two reaction tanks comprise a first reaction tank and a second reaction tank, wherein a part of the fermentation liquid is continuously transferred from the first reaction tank to the second reaction tank.

11. The method for producing ethanol according to claim 2, wherein a mass ratio of the addition amount of the additional saccharification enzyme per day to the initial content of the saccharification enzyme in the fermentation liquid is 1:15 to 1:50.

12. The method for producing ethanol according to claim 2, wherein the additional saccharification enzyme is added to the fermentation liquid in an amount of 20 U/L or less.

13. The method for producing ethanol according to claim 2, wherein the additional saccharification enzyme is intermittently added every 2 to 192 hours.

14. The method for producing ethanol according to claim 2, wherein the concentration of the lignocellulosic raw material in the fermentation liquid is adjusted so as to be maintained within a predetermined range.

15. The method for producing ethanol according to claim 1, wherein the multiple parallel fermentation is performed in at least two reaction tanks connected to each other, and the solid content concentrated fermentation liquid is transferred to a first reaction tank which stores the fermentation liquid and in which additional lignocellulosic raw material is continuously fed.

16. The method for producing ethanol according to claim 1, wherein an average retention time is 12 to 240 hours.

* * * * *